United States Patent
Nishimura et al.

(10) Patent No.: US 10,632,065 B2
(45) Date of Patent: *Apr. 28, 2020

(54) MICRONEEDLE DEVICE CONTAINING RECOMBINANT FOLLICLE STIMULATING HORMONE

(71) Applicants: HISAMITSU PHARMACEUTICAL CO., INC., Tosu-shi, Saga (JP); ASKA Pharmaceutical Co., Ltd., Minato-ku, Tokyo (JP)

(72) Inventors: Shinpei Nishimura, Tsukuba (JP); Seiji Tokumoto, Tsukuba (JP); Takeshi Ito, Kawasaki (JP); Hajime Asada, Kawasaki (JP)

(73) Assignees: HISAMITSU PHARMACEUTICAL CO., INC., Tosu-Shi, Saga (JP); ASKA PHARMACEUTICAL CO., LTD., Minato-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/521,101

(22) PCT Filed: Oct. 19, 2015

(86) PCT No.: PCT/JP2015/079462
§ 371 (c)(1),
(2) Date: Apr. 21, 2017

(87) PCT Pub. No.: WO2016/067956
PCT Pub. Date: May 6, 2016

(65) Prior Publication Data
US 2017/0348228 A1    Dec. 7, 2017

(30) Foreign Application Priority Data

Oct. 27, 2014    (JP) .................................. 2014-218549

(51) Int. Cl.
*A61K 9/00* (2006.01)
*A61K 38/24* (2006.01)
(Continued)

(52) U.S. Cl.
CPC .............. *A61K 9/0021* (2013.01); *A61K 9/00* (2013.01); *A61K 38/24* (2013.01); *A61K 47/02* (2013.01);
(Continued)

(58) Field of Classification Search
None
See application file for complete search history.

(56) References Cited

U.S. PATENT DOCUMENTS

2005/0025778 A1    2/2005  Cormier et al.
2006/0040864 A1    2/2006  Ameri et al.
(Continued)

FOREIGN PATENT DOCUMENTS

EP    3192556 A1    7/2017
JP    2523843 B2    5/1996
(Continued)

OTHER PUBLICATIONS

International Search Report dated Oct. 27, 2015 corresponding to application No. PCT/JP2015/075729.
(Continued)

*Primary Examiner* — Elizabeth C. Kemmerer
(74) *Attorney, Agent, or Firm* — Nath, Goldberg & Meyer; Joshua B. Goldberg

(57) ABSTRACT

The present invention provides a microneedle device comprising: a substrate; a microneedle disposed on the substrate; and a coating layer formed on the microneedle; in which the coating layer comprises a recombinant follicle-stimulating hormone, arginine, and glycerin, in the coating layer, the mass of arginine is 0.07 to 0.75-fold of the mass of the
(Continued)

recombinant follicle-stimulating hormone and the mass of glycerin is 0.1 to 2.75-fold of the mass of the recombinant follicle-stimulating hormone.

4 Claims, 4 Drawing Sheets

(51) Int. Cl.
    *A61K 47/02*     (2006.01)
    *A61K 47/10*     (2017.01)
    *A61K 47/12*     (2006.01)
    *A61K 47/18*     (2017.01)
    *A61M 37/00*     (2006.01)

(52) U.S. Cl.
    CPC ............... *A61K 47/10* (2013.01); *A61K 47/12* (2013.01); *A61K 47/18* (2013.01); *A61K 47/183* (2013.01); *A61M 37/0015* (2013.01); *A61M 2037/0023* (2013.01); *A61M 2037/0053* (2013.01)

(56) References Cited

U.S. PATENT DOCUMENTS

| | | | |
|---|---|---|---|
| 2006/0188555 | A1 | 8/2006 | Cormier et al. |
| 2008/0108557 | A1 | 5/2008 | Behrens et al. |
| 2009/0291473 | A1 | 11/2009 | Sugimura et al. |
| 2011/0190688 | A1 | 8/2011 | Tagliaferri et al. |
| 2011/0288485 | A1 | 11/2011 | Tokumoto et al. |
| 2012/0330250 | A1 | 12/2012 | Kuwahara et al. |
| 2013/0123707 | A1* | 5/2013 | Determan ............ A61K 9/0021 604/173 |
| 2013/0323293 | A1 | 12/2013 | Umemoto et al. |
| 2014/0066842 | A1 | 3/2014 | Zhang et al. |
| 2014/0066843 | A1 | 3/2014 | Zhang et al. |
| 2015/0314117 | A1 | 11/2015 | Arami et al. |
| 2015/0374620 | A1 | 12/2015 | Sugahara et al. |
| 2017/0266427 | A1* | 9/2017 | Nishimura ........ A61M 37/0015 |

FOREIGN PATENT DOCUMENTS

| | | |
|---|---|---|
| JP | 2001-323000 A | 11/2001 |
| JP | 2007-521092 A | 8/2007 |
| JP | 2008-510520 A | 4/2008 |
| JP | 2008-528509 A | 7/2008 |
| JP | 2009-273427 A | 11/2009 |
| JP | 2011-516166 A | 5/2011 |
| JP | 2013-107885 A | 6/2013 |
| JP | 2014-507473 A | 3/2014 |
| JP | 2014-514022 A | 6/2014 |
| TW | 201611859 A | 4/2016 |
| WO | 8810270 A1 | 12/1988 |
| WO | 2010074239 A1 | 7/2010 |
| WO | 2011105496 A1 | 9/2011 |
| WO | 2012115207 A1 | 8/2012 |
| WO | 2012115208 A1 | 8/2012 |
| WO | 2012/122163 A1 | 9/2012 |
| WO | 2013082418 A1 | 6/2013 |
| WO | 2014097837 A1 | 6/2014 |
| WO | 2014126104 A1 | 8/2014 |

OTHER PUBLICATIONS

International Search Report dated Dec. 22, 2015 corresponding to application No. PCT/JP2015/079462.
International Preliminary Report on Patentability dated May 11, 2017 corresponding to WO Patent application No. PCT/JP2015/079462.
The Extended European Search Report dated May 24, 2018 corresponding to application No. 15855242.2-1114.
Office Action dated Oct. 15, 2018 corresponding to Taiwanese application No. 104134889.

* cited by examiner (a)

(b)

(c)

MICRONEEDLE DEVICE CONTAINING RECOMBINANT FOLLICLE STIMULATING HORMONE

This is a National Phase Application filed under 35 U.S.C. 371 as a national stage of PCT/JP2015/079462, filed Oct. 19, 2015, an application claiming the benefit of Japanese Application No. 2014-218549, filed Oct. 27, 2014, the content of each of which is hereby incorporated by reference in its entirety.

TECHNICAL FIELD

The present invention relates to a microneedle device containing a recombinant follicle-stimulating hormone.

BACKGROUND ART

A microneedle device is known as one of the devices for intradermal administration of a physiologically active substance. The microneedle device has a plurality of microneedles on its main surface. As one specific aspect thereof, for example, there is a microneedle having a coating layer containing a physiologically active substance formed thereon and a self-dissolving microneedle containing a physiologically active substance (for example, Patent Literatures 1 and 2).

CITATION LIST

Patent Literature

Patent Literature 1: JP 2008-528509 A
Patent Literature 2: JP 2014-507473 A

SUMMARY OF INVENTION

Technical Problem

The present inventors have found that in the case that a microneedle is coated and a recombinant follicle-stimulating hormone is used as a physiologically active substance, the content uniformity of the recombinant follicle-stimulating hormone in the coating process is low, and the recombinant follicle-stimulating hormone tends to aggregate during storage of the microneedle device.

When the content uniformity of the physiologically active substance in the coating process is low, the absorption of the recombinant follicle-stimulating hormone is not stable during the use of the microneedle device. Consequently, a sufficient therapeutic effect may not be obtained.

Therefore, an object of the present invention is to provide a microneedle device having a coating layer which is coated with a recombinant follicle-stimulating hormone so as to hardly aggregate in the coating layer and uniformly disperse.

Solution to Problem

The present invention provides a microneedle device comprising: a substrate; a microneedle disposed on the substrate; and a coating layer formed on the microneedle; wherein the coating layer comprises a recombinant follicle-stimulating hormone (hereinafter, also simply referred to as "FSH"), arginine, and glycerin, wherein, in the coating layer, the mass of arginine is 0.07 to 0.75-fold, preferably 0.07 to 0.6-fold of the mass of FSH and the mass of glycerin is 0.1 to 2.75-fold of the mass of FSH.

When the coating layer contains FSH, arginine, and glycerin, an effective amount of FSH can be continuously administered to a user, the content uniformity and solubility of FSH are also excellent, and the dripping of the coating layer is less likely caused.

It is preferable that the coating layer further comprises an acid selected from the group consisting of citric acid, phosphoric acid, boric acid, tartaric acid, and lactic acid.

Further, the present invention provides a method for producing a microneedle device including the steps of: providing a microneedle array having a substrate and a microneedle; mixing a FSH, arginine, and glycerin to obtain a coating composition; coating the microneedle with the coating composition; and drying the coating composition to form a coating layer on the microneedle.

In the case of the coating composition in the production method, the mass of arginine is 0.07 to 0.75-fold and preferably 0.07 to 0.6-fold of the mass of FSH, and the mass of glycerin is preferably 1 to 3-fold of the mass of FSH.

It is preferable that the coating composition further comprises an acid selected from the group consisting of citric acid, phosphoric acid, boric acid, tartaric acid, and lactic acid.

The drying is preferably performed until, in the coating layer, the mass of arginine reaches 0.07 to 0.75-fold and preferably 0.07 to 0.6-fold of the mass of FSH, and the mass of glycerin reaches 0.1 to 2.75-fold of the mass of FSH.

Further, the present invention provides a coating agent for microneedles which contains FSH, arginine, and glycerin and in which, in the coating agent, the content of arginine is 0.07 to 0.75-fold and preferably 0.07 to 0.6-fold of the mass of FSH and the content of glycerin is 1 to 3-fold of the mass of FSH.

The coating agent preferably comprises an acid selected from the group consisting of citric acid, phosphoric acid, boric acid, tartaric acid, and lactic acid.

Advantageous Effects of Invention

According to the microneedle device of the present invention, when the coating layer comprises FSH, arginine, and glycerin, an effective amount of FSH can be continuously administered to a user, the content uniformity and solubility of FSH are also excellent, and the dripping of the coating layer is less likely to occur.

DESCRIPTION OF EMBODIMENTS

Figure 1:
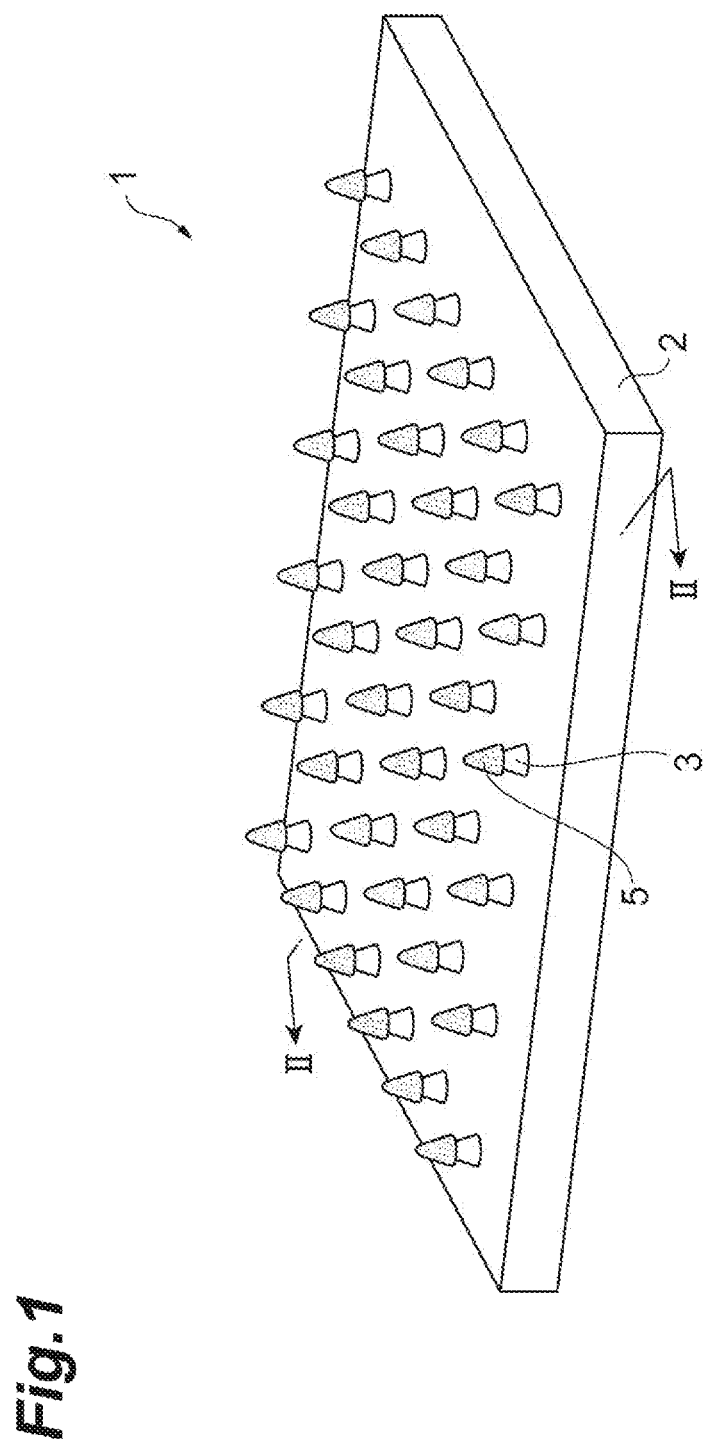
FIG. 1 is a perspective view showing one embodiment of a microneedle device.

Hereinbelow, preferable embodiments will be explained with reference to drawings. It is to be noted that in the explanation of the drawings, the same symbols are assigned to the same elements and redundant explanation will be omitted. Also, in the drawings, some parts are exaggeratedly drawn to make understanding easy, and thus the size and ratio are not necessarily consistent with the description.

One embodiment of the present invention is a microneedle device comprising: a substrate; a microneedle disposed on the substrate; and a coating layer formed on the microneedle; wherein the coating layer contains a FSH, arginine, and glycerin.

FIG. 1 is a perspective view showing one embodiment of a microneedle device. A microneedle device 1 shown in FIG. 1 has a substrate 2, a plurality of microneedles 3 that are two-dimensionally arranged on the substrate 2, and a coating layer 5 formed on each of the microneedles 3. The coating layer 5 contains a FSH, arginine, and glycerin.

The substrate 2 is a foundation to support the microneedles 3. The area of the substrate 2 is preferably 0.5 to 10 cm$^2$, more preferably 1 to 5 cm$^2$, and still more preferably 1 to 3 cm$^2$. A substrate of a desired size may be configured by connecting a plurality of the substrates 2.

The microneedles 3 each have a minute structure, and the height (length) thereof is preferably 50 to 600 μm. At this point, the length of the microneedles 3 is set at 50 μm or more, thereby ensuring administration of the FSH contained in the coating layer. Further, the length of the microneedles 3 is set at 600 μm or less, thereby avoiding that the microneedles contact nerves so as to reduce the possibility of pain and avoid the possibility of bleeding. Also, when the length of the microneedles 3 is 500 μm or less, the amount of the FSH to enter the skin can be efficiently administered, and in certain cases, administrating without piercing the basement membrane is also possible. The length of the microneedles 3 is particularly preferably 300 to 500 μm.

At this point, a microneedle 3 refers to a projecting structure including, in a broad sense, a needle shape or a structure including a needle shape. However, the microneedle is not limited to a structure of a needle shape having a tapered tip, and may also be a structure lacking a tapered tip. When the microneedles 3 each have a conical structure, the diameter of the basal surface thereof is preferably about 50 to 200 μm. Although the microneedles 3 are each in a conical shape according to the present embodiment, microneedles may be in a polygonal pyramid shape such as a square pyramid or in other shapes.

The microneedles 3 are each typically disposed spaced apart so as to have a density of approximately 1 to 10 needles per millimeter (mm) in a row of the needles. Generally, adjacent rows are spaced apart from each other by a distance substantially equal to the space between the needles in a row, and the microneedles 3 have a needle density of 100 to 10000 needles per cm$^2$. When a needle density of 100 needles or more is achieved, the microneedles can efficiently pierce the skin. Meanwhile, a needle density of more than 10000 needles makes it difficult to maintain the strength of the microneedles 3. The density of the microneedles 3 is preferably 200 to 5000 needles, more preferably 300 to 2000 needles, and still more preferably 400 to 850 needles.

Examples of a material of the substrate 2 or the microneedles 3 include silicon, silicon dioxide, ceramics, metals (such as stainless steel, titanium, nickel, molybdenum, chromium, and cobalt) and synthetic or natural resin materials. In consideration of the antigenicity of the microneedles and the unit price of the material, a biodegradable polymer such as polylactic acid, polyglycolide, polylactic acid-co-polyglycolide, pullulan, caprolactone, polyurethane, and polyanhydride, and a synthetic or natural resin material such as polycarbonate, polymethacrylic acid, ethylenevinyl acetate, polytetrafluoroethylene, and polyoxymethylene, which are non-degradable polymers, are particularly preferable. Further, polysaccharides such as hyaluronic acid, sodium hyaluronate, pullulan, dextran, dextrin, and chondroitin sulfate are also suitable.

Examples of a production method of the substrate 2 or the microneedles 3 include wet etching process or dry etching process using a silicon substrate, precision machining using metals or resins (such as electric discharge method, laser processing, dicing processing, hot embossing process, and injection mold processing), and machinery cutting. By these processing methods, the substrate 2 and the microneedles 3 are integrally molded. Examples of a method for hollowing the microneedles 3 include a method in which a secondary processing such as laser processing is applied after producing the microneedles 3.

Although the microneedle device 1 has the coating layer 5 on each of the microneedles 3, the coating layer 5 is preferably formed by coating with the coating composition. Examples of the coating method include spray coating and dip coating, and the dip coating is preferable. In this regard, although the coating layer 5 is formed on all the microneedles 3 in FIG. 1, the coating layer 5 may be formed on only some of the microneedles 3. Although the coating layer 5 is formed on only the tip portion of the microneedle 3 in FIG. 1, the layer may be formed so as to cover the whole microneedle 3. Further, the coating layer 5 may be formed on the substrate 2.

Figure 2:
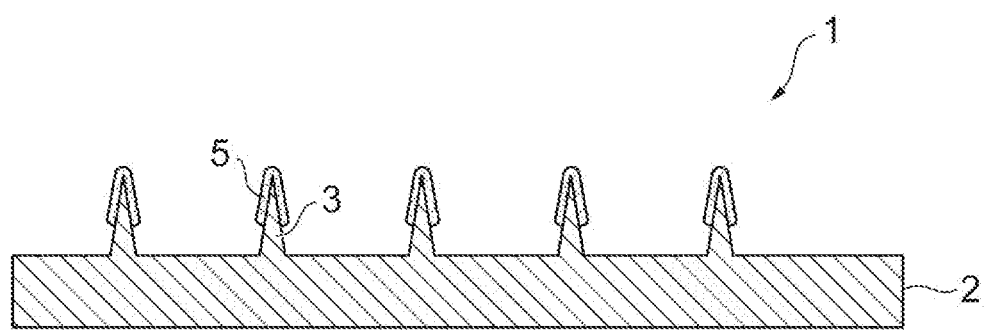
FIG. 2 is a cross-sectional side surface view of FIG. 1 taken along the line II-II.

FIG. 2 is a cross-sectional side surface view of FIG. 1 taken along the line II-II. As shown in FIG. 2, the microneedle device 1 has the substrate 2, the microneedles 3 disposed on the substrate 2, and the coating layer 5 formed on each of the microneedles 3. The coating layer 5 formed on each of the microneedles contains a FSH, arginine, and glycerin.

The mass of arginine contained in the coating layer is preferably 0.07 to 0.75-fold, more preferably 0.07 to 0.6-fold, still more preferably 0.07 to 0.3-fold, and particularly preferably 0.08 to 0.15-fold of the mass of FSH.

The lower limit of the mass of glycerin contained in the coating layer is preferably 0.1-fold, more preferably 0.25-fold, and still more preferably 0.5-fold of the mass of FSH. Further, the upper limit of the mass of glycerin contained in the coating layer is preferably 2.75-fold, more preferably 1.6-fold, and still more preferably 1-fold of the mass of FSH.

Further, preferred is a case in which the content of glycerin is 40% by mass or less based on the total mass of the coating layer, because the dripping is less likely to occur.

The coating layer can be formed using, for example, a coating composition containing FSH, arginine, and glycerin. The coating layer contains FSH, arginine, and glycerin so that deterioration with time of the coating layer can be suppressed when applying the coating composition or storing the microneedle device.

The recombinant follicle-stimulating hormone of the present invention is a glycoprotein produced by the anterior pituitary gonadotroph, and is a recombinant type of follicle stimulating hormone which is a kind of gonadotrophic hormones (gonadotropin). In males, FSH promotes seminiferous-tubule growth in the testis and maintains spermatogenesis. In females, FSH promotes follicle growth in the ovary.

Similarly to a natural follicle stimulating hormone, the structure of FSH is a heterodimer glycoprotein composed of α and β chains bound by a non-covalent bond, and each of the α and β chains is saccharified, namely, glycosylated. The α-subunit consists of 92 amino acid residues, the β-subunit consists of 111 amino acid residues, and the subunits has two potential glycosylation sites bound to asparagines.

FSH can be obtained by, for example, culturing recombinant human FSH-producing cells produced by transfecting an expression vector having human FSH α-chain cDNA incorporated therein and an expression vector having human FSH β-chain cDNA incorporated therein with mammalian cells in a serum free medium so as to allow the FSH to secrete in the culture medium, and purifying the FSH from the culture medium.

After removing recombinant human FSH producing cells from the culture medium, FSH is purified by recovering FSH active fractions using a combination of cation-exchange column chromatography, dye-affinity column chromatography, reverse phase column chromatography, phenyl-sepharose column chromatography or gel-filtration column chromatography. Thus, highly pure FSH can be obtained (for example, JP 2523843 B and JP 2001-323000 A and JP 2009-273427 A). The resulting FSH is highly useful since recombinant human FSH producing cells are cultured in a serum free medium, thereby preventing the contamination of viruses.

The purified FSH is subjected to SDS-PAGE electrophoresis under non-reductive and non-heat conditions, followed by staining the resulting gel with coomassie. Then, a single band is observed at a molecular weight of about 45 kDa. This band is stained by Western blotting using an anti human FSH antibody.

Further, the purified FSH is analyzed by isoelectric focusing electrophoresis and a multiple of bands at isoelectric points (pIs) of 3.5 to 5.5 is observed.

FSH administration results in induction of ovulation in anovulation or infrequent ovulation associated with hypothalamic-pituitary dysfunction or polycystic ovary syndrome. Therefore, the use of the microneedle device of the embodiment is effective in treating anovulation, infrequent ovulation or infertility associated with hypothalamic-pituitary dysfunction or polycystic ovary syndrome.

The content of FSH in the coating composition is preferably 21 to 39% by mass, more preferably 29 to 37% by mass, and still more preferably 30 to 35% by mass based on the total mass of the coating composition. When the content of FSH is 21% by mass or more, a pharmacologic action of FSH is sufficiently exerted, thereby easily producing a desired therapeutic effect.

Further, the coating composition further contains arginine, which makes FSH less likely to aggregate in the applied coating composition. The formation of FSH aggregates causes a decrease in the amount of FSH which can contribute to the therapy, thereby hardly obtaining a desired therapeutic effect.

The content of arginine in the coating composition is preferably 0.07 to 0.75-fold, more preferably 0.07 to 0.6-fold, still more preferably 0.07 to 0.3-fold, and particularly preferably 0.08 to 0.15-fold of the mass of FSH contained in the coating composition. When the content of arginine is 0.07-fold or more of the mass of FSH, FSH aggregates are hardly formed in the coating composition or the coating layer. Further, the content of arginine is 0.75-fold or less (particularly, 0.6-fold or less), thereby further improving the solubility of FSH in the coating composition.

The coating composition contains glycerin so that the content uniformity of FSH is improved when microneedles are coated with the coating composition. The content uniformity of FSH is improved, whereby FSH is stably released from the coating layer during the use of the microneedle device and a desired therapeutic effect can be continuously obtained. Further, since glycerin has a high solubility of FSH, it is suitable as a component of the coating composition.

The content of glycerin in the coating composition is preferably 1 to 3-fold, more preferably 1 to 2.75-fold, still more preferably 1 to 1.8-fold, and particularly preferably 1 to 1.2-fold of the mass of FSH contained in the coating composition. More preferred is a case in which the content of glycerin is 1-fold or more of the mass of FSH, because the content uniformity and solubility of the FSH in the coating layer are excellent and the dripping is less likely to occur when being applied to microneedles.

Further, the coating composition preferably contains an acid selected from the group consisting of citric acid, phosphoric acid, boric acid, tartaric acid, and lactic acid. Particularly, the coating composition more preferably contains citric acid. The coating composition contains a specific acid so that the formation of FSH aggregates tends to be further suppressed.

In the case of the coating composition containing citric acid, phosphoric acid, boric acid, tartaric acid or lactic acid, the formation of FSH aggregates tends to be further suppressed, compared to the case of the coating composition containing hydrochloric acid, sulfuric acid or acetic acid.

The content of the acid is preferably 1 to 6% by mass, more preferably 1 to 3.5% by mass, and still more preferably 1 to 2% by mass based on the total mass of the coating composition.

The content of the acid is preferably 0.2 to 0.6-fold, more preferably 0.3 to 0.6-fold, and still more preferably 0.3 to 0.4-fold of the mass of the arginine contained in the coating composition.

The coating composition may further contain a solvent, a polymeric carrier (thickening agent), a solubilizing aid, an absorption promoter, a stabilizer, an antioxidant, an emulsifier, a surfactant, and other components such as salts, as needed. Examples of the solvent include water such as purified water and distilled water; and alcohols such as methanol and ethanol. The coating composition contains a solvent so that the handling properties when applied to microneedles can be improved and the solvent can be easily removed by the drying step.

When the coating composition contains a solvent, the solvent is removed in the drying step. Accordingly, the composition ratio of the components in the coating composition is not necessarily reflected in the coating layer.

Hence, a coating layer is formed by drying the coating composition applied to microneedles when a microneedle device is produced. In the drying step, the solvent contained in the coating composition is removed and glycerin evaporates, as a result of which the content of glycerin may also decrease. Glycerin itself is not converted to a solid by, for example, drying under reduced pressure at ordinary temperature.

Examples of the polymeric carrier include polyethylene oxide, polyhydroxymethylcellulose, hydroxypropylcellulose, polyhydroxypropylmethylcellulose, polymethylcellulose, dextran, polyethylene glycol, polyvinyl alcohol, polyvinylpyrrolidone, pullulan, carmellose sodium, chondroitin sulfate, hyaluronic acid, dextran, and gum arabic. The weight average molecular weight of polyethylene glycol to be used as a polymeric carrier preferably exceeds 600 but is 500000 or less. As the polymeric carrier, a carrier highly compatible (having properties of being uniformly mixed) with a physiologically active substance is preferable. Particularly preferred are hydroxypropylcellulose, dextran, polyvinyl alcohol, pullulan, and the like.

The content of the polymeric carrier in the coating composition 10 is 0.005 to 30% by mass, preferably 0.01 to 20% by mass, and more preferably 0.05 to 10% by mass based on the total mass of the coating composition 10. The polymeric carrier may need to have a certain degree of viscosity that does not cause dripping and the viscosity is preferably 100 to 100000 mPa·s at room temperature (25° C.). A more preferable viscosity is 500 to 60000 mPa·s.

In addition to the above, to the coating composition 10, propylene carbonate, crotamiton, L-menthol, peppermint oil, limonene, diisopropyl adipate, and the like may be added as a solubilizing aid or absorption promoter, and methyl salicylate, glycol salicylate, L-menthol, thymol, peppermint oil, nonylic acid vanillylamide, chili pepper extract, and the like may be added as an efficacy supplement as needed.

The surfactant may be either a nonionic surfactant or an ionic surfactant (cationic, anionic, and amphoteric); however, from the safety aspect, a nonionic surfactant, which is normally used for a pharmaceutical base, is desirable. Examples of these compounds include sugar alcohol fatty acid ester such as sucrose fatty acid ester, propylene glycol fatty acid ester, polyoxyethylene sorbitan fatty acid ester, polyoxyethylene glycerin fatty acid ester, polyethylene glycol fatty acid ester, polyoxyethylene castor oil, and polyoxyethylene hydrogenated castor oil.

A method for producing a microneedle device comprises the steps of: providing a microneedle array that has a substrate and a microneedle; mixing a FSH, arginine, and glycerin to obtain a coating composition; coating the microneedle with the coating composition; and drying the coating composition to form a coating layer on the microneedle.

As for the drying conditions to form a coating layer, the drying is performed until, in the coating layer, the mass of arginine reaches 0.07 to 0.75-fold and preferably 0.07 to 0.6-fold of the mass of FSH, and the mass of glycerin reaches 0.1 to 2.75-fold of the mass of FSH. In this regard, the lower limit of the mass of glycerin in the coating layer is preferably 0.1-fold, more preferably 0.25-fold, and still more preferably 0.5-fold of the mass of FSH. The upper limit of the mass of glycerin in the coating layer is preferably 2.75-fold, more preferably 1.6-fold, and still more preferably 1-fold of the mass of FSH.

Under the drying conditions, the decompression degree, temperature, and time can be appropriately adjusted, and it is preferable to perform the adjustment so that the mass of arginine and the mass of glycerin are within the above range. The drying can be performed, for example, under the following drying conditions: decompression degree of 1 to 100 Pa, temperature of 0 to 40° C., and time of 1 hour to 100 hours. The drying is preferably performed at a decompression degree of 5 to 20 Pa and room temperature for 10 to 50 hours. More specifically, for example, the drying conditions are as follows: room temperature and 10 Pa.

Subsequently, the method for producing a microneedle device will be explained with reference to FIGS. 3(a) to 3(c). In this regard, the production method shown in FIGS. 3(a) to 3(c) is also referred to as "dip method using a mask plate".

Figure 3:
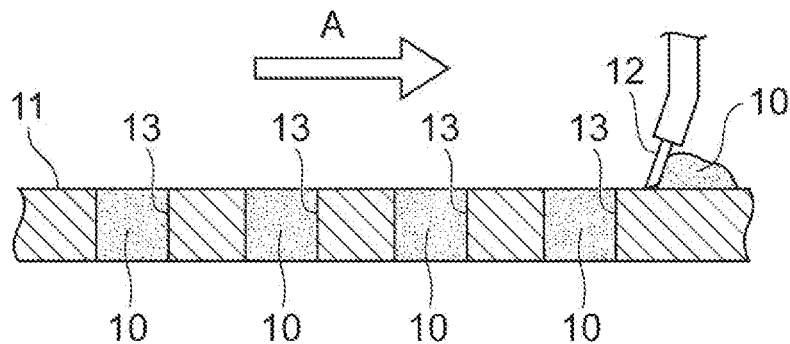
FIGS. 3(a) to 3(c) are pattern diagrams showing one embodiment of a method for producing a microneedle device.
Figure 3:
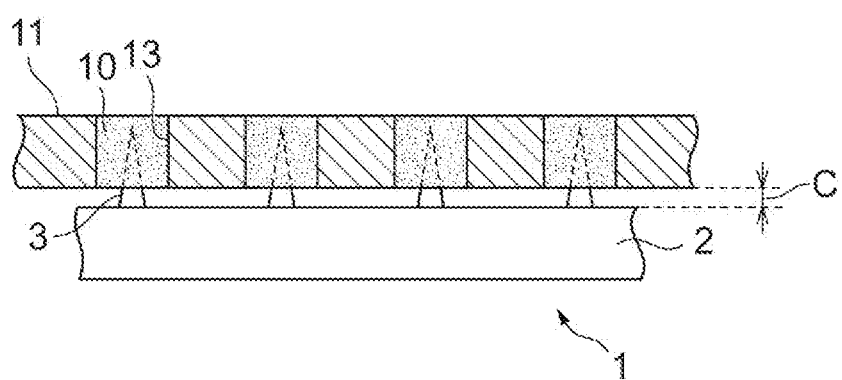
Figure 3:
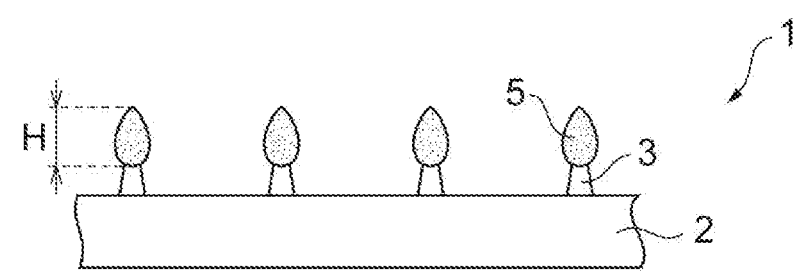

FIGS. 3(a) to 3(c) are pattern diagrams showing one embodiment of a method for producing a microneedle device. According to this method, first of all, as shown in FIG. 3(a), the coating composition 10 is swept with a spatula 12 in the direction of the arrow A on a mask plate 11. By doing so, openings 13 are filled with the coating composition 10. Subsequently, as shown in FIG. 3(b), the microneedles 3 are inserted into the openings 13 of the mask plate 11. Thereafter, as shown in FIG. 3(c), the microneedles 3 are pulled out from the openings 13 of the mask plate 11. By doing so, the coating composition 10 adheres to the microneedles 3. In this regard, the coating composition 10 may adhere to the substrate 2. The volatile substance in the coating composition 10 on the microneedles 3 is removed by a method such as air drying, vacuum drying, or a combination of these methods. By the above process, the coating layer 5 strongly adheres to each of the microneedles 3, and typically becomes glassy or solid, whereby the microneedle device 1 is produced. The water content in the coating layer 5 is normally 55% by mass or less, preferably 30% by mass or less, and more preferably 10% by mass or less based on the total amount of the coating layer 5. By the above method, dripping of the coating composition 10 after being coated is prevented. The dripping indicates dripping of the coating composition from needle tips and means that an H part in FIG. 3(c) lengthens.

The height H of the coating layer 5 formed on each of the microneedles 3 is adjusted by a clearance (gap) C shown in FIG. 3(b). This clearance C is defined as a distance between the basal surface of the microneedles 3 and the surface of the mask plate 11 (a thickness of the substrate 2 is not involved), and is set according to a tension of the mask plate 11 and the length of the microneedles 3. The range of the distance of clearance C is preferably 0 to 500 µm. When a distance of clearance C is 0, it means that the coating composition 10 is applied to the entire microneedles 3. Although the height H of the coating composition 10 formed on the microneedles 3 varies depending on the height H of the microneedles 3, the height H is normally 10 to 500 µm, preferably 30 to 300 µm, and more preferably 40 to 250 µm. In order to effectively administer the FSH in the coating composition 10 to the skin, the substance is preferably concentrated in a part of the microneedle 3 (i.e., the tip portion of the microneedle 3). From viewpoints of the stimulation to the skin and the transferring efficiency of FSH to the skin, the FSH is evenly located, preferably at up to 200 µm, more preferably at up to 150 µm, and still more preferably at up to 120 µm from the tip of the microneedle 3. When the coating composition 10 has a high viscosity, the coating layer 5 is easily formed on a part of the microneedle. By the method, the coating composition 10 adhering to the microneedles 3 after removal of its volatile components can form preferably an approximately spherical or teardrop shaped coating layer 5 at the tip portion of the microneedle 3. Then, the coating composition is inserted into the skin at the same time when the microneedles 3 pierce the skin.

The thickness of the dried coating layer 5 is preferably less than 50 µm, more preferably less than 40 µm, and still more preferably 1 to 30 µm. Generally, the thickness of the coating layer 5 refers to an average thickness as measured over the surface of the microneedle 3 after drying. The thickness of the coating layer 5 can be optionally increased by applying a plurality of films of the coating composition 10, namely, by repeatedly performing the step of coating with the coating composition 10.

When the microneedle 3 is coated with the coating composition 10, temperature and humidity in an installation environment of an apparatus are preferably controlled at a constant level. When the coating composition 10 contains water, the environment may be filled with water, as needed. By doing so, evaporation of the water in the coating composition 10 can be prevented as much as possible.

The formation of aggregates can be suppressed by the coating composition according to the present embodiment. In the evaluation of the content rate of aggregates, the coating composition is separated using chromatography and the content rate of aggregates can be calculated from a peak area. The method for evaluating the content rate of aggregates is, for example, a method including the steps of: extracting aggregates from the coating composition applied to microneedles using a phosphate buffer containing 0.01% polysorbate 80; separating the obtained extract using size exclusion chromatography; and evaluating proteins as aggregates contained in the fractions whose retention time is shorter than that of FSH.

The method for using the microneedle device of the present invention in therapy is, for example, a method for allowing the microneedle device to collide with or adhere to the surface of the skin of a user using the apparatus described in WO 2014/097837. Specifically, at least a part of the tip of the microneedle is inserted into the skin, and the recombinant FSH may be absorbed to the body of the user from the coating at a portion into which the microneedle is inserted. After maintaining the state in which the recombinant FSH may be absorbed to the body of the user, the microneedle device is removed from the surface of the skin. The time (piercing time) required to maintain the state with the microneedle inserted into the skin may be within 10 minutes, 1 minute, 30 seconds or 10 seconds, or may be 0.5 second or longer.

From the viewpoint of reducing the burden on the user, a shorter piercing time is preferred. As the piercing time becomes longer, there is an increased risk of damaging the dermal tissue or causing a small amount of bleeding of the skin.

For example, there is provided a method for administering recombinant FSH comprising a step of applying a microneedle device which includes a coating layer formed by coating the tip of the microneedle with the composition containing the recombinant FSH (30 to 600 IU) to the skin of a user by the above method (piercing time, for example, 0.5 second to 1 minute). The time (Tmax) required until the concentration of FSH in the plasma reaches a maximum after applying the microneedle device is, for example, about 3 to 8 hours. Taking into consideration that endogenous hormone is physiologically released in pulses, it is assumed that when the Tmax is within the above range, the microneedle device easily exerts an expected drug efficacy and side effects are less likely to occur.

EXAMPLES

Hereinbelow, the present invention will be more specifically described by providing Examples.

(1) Content Uniformity Test 1

The coating agents of Reference Examples 1 to 3 prepared according to the description of Table 1 were applied to microneedles. Each number in Table 1 means mass percent relative to the whole coating agent.

Subsequently, the coating agents of Reference Examples 1 and 2 were applied to ten sheets at an RH of about 40%, and the coating agent of Reference Example 3 was applied to twenty sheets at an RH of 90%. The coating agents applied to microneedles were individually recovered. The content of recombinant follicle-stimulating hormone (hereinafter, simply referred to as "FSH") in each of the coating agents was measured. The average, standard deviation (SD), and coefficient of variation (CV) of the content of the resulting FSH were calculated. In this regard, the coefficient of variation (CV) is a value obtained by dividing the standard deviation by the average.

TABLE 1

|  |  | Reference Example 1 | Reference Example 2 | Reference Example 3 |
|---|---|---|---|---|
|  | FSH | 40 | 40 | 40 |
| Base material | Glycerin | 60 | — | — |
|  | Propylene glycol | — | 60 | — |
|  | Pullulan | — | — | 15 |
|  | Water | — | — | 55 |
|  | Total | 100 | 100 | 100 |

The results are shown in Table 2. The coating agent of Reference Example 1 containing glycerin had a coefficient of variation of 7.2 and had a small variation in content, compared to the coating agent of Reference example 2 containing propylene glycol and the coating agent of Reference Example 3 containing pullulan.

TABLE 2

|  | Reference Example 1 | Reference Example 2 | Reference Example 3 |
|---|---|---|---|
| Environmental humidity for coating | 40% RH | 40% RH | 90% RH |
| Average [μg] | 58.2 | 78.1 | 21.9 |
| Standard deviation (SD) [μg] | 4.2 | 23.1 | 4.5 |
| Coefficient of variation (CV) [%] | 7.2 | 29.6 | 20.5 |

(2) Aggregation Test 1

Coating agents of Reference Examples 4 to 7 and Example 1 were prepared according to the description of Table 3. Each of the obtained coating compositions was applied to the tip of each microneedle in the microneedle array by the dip method using a mask plate, and the microneedle array was dried under reduced pressure. Subsequently, the obtained microneedle device was packed and stored at 40° C. for two weeks. Thereafter, the content rate of aggregates was evaluated in the following manner. In this regard, no protein was contained in the fraction whose retention time was longer than that of FSH.

<Method for Evaluating Content Rate of Aggregates>

Extraction was performed from the coating composition applied to microneedles using a phosphate buffer containing 0.01% polysorbate 80. The obtained extract was separated using size exclusion chromatography, followed by evaluating proteins (as aggregates) contained in the fractions whose retention time was shorter than that of FSH.

TABLE 3

|  | Reference Example 4 | Reference Example 5 | Reference Example 6 | Reference Example 7 | Example 1 |
|---|---|---|---|---|---|
| FSH | 33.3 | 31 | 31 | 31 | 31 |
| Glycerin | 53.3 | 49.7 | 49.7 | 49.7 | 49.7 |
| Trehalose | — | 5.5 | — | — | — |
| Glucose | — | — | 5.5 | — | — |
| Maltose | — | — | — | 5.5 | — |
| Arginine/citric acid | — | — | — | — | 5.5 |
| Purified water | 13.3 | 13.8 | 13.8 | 13.8 | 13.8 |
| Total | 99.9 | 100 | 100 | 100 | 100 |

Figure 4:
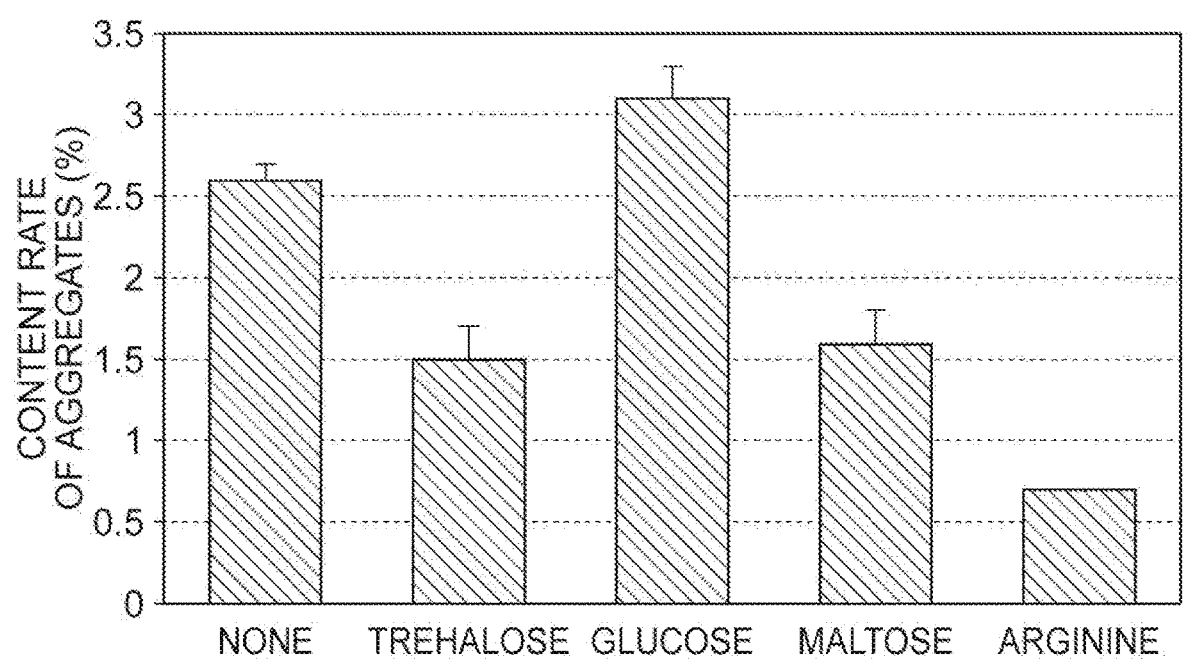
FIG. 4 is a graph showing the content rate of FSH aggregates in a coating layer of a microneedle device of one embodiment.

The results are shown in FIG. 4. As shown in FIG. 4, the coating composition of Example 1 obtained by using arginine and citric acid was excellent in terms of suppressing formation of FSH aggregates.

(3) Aggregation Test 2

FSH, glycerin, arginine, acid, and purified water were mixed according to the description of Table 4 to prepare coating compositions having a pH of 8. 5N hydrochloric acid, phosphoric acid, 5N sulfuric acid, boric acid, citric acid, tartaric acid, acetic acid, and lactic acid were used as acids. Each of the obtained coating compositions was applied to the tip of each microneedle in the microneedle array by the dip method using a mask plate, and the microneedle array was dried under reduced pressure. Subsequently, the obtained microneedle device was packed and stored at 40° C. for two weeks. Thereafter, the content rate of aggregates was evaluated. In this regard, the content rate of aggregates was evaluated in a similar manner to Aggregation Test 1.

TABLE 4

|  |  | Example 2 | Example 3 | Example 4 | Example 5 |
|---|---|---|---|---|---|
|  | FSH | 33.6 | 33.6 | 33.6 | 33.6 |
|  | Glycerin | 38.6 | 40.3 | 37.3 | 40.2 |
|  | Arginine | 4.5 | 4.5 | 4.5 | 4.5 |
| Acid | 5N hydrochloric acid | 4 | — | — | — |
|  | Phosphoric acid | — | 1.4 | — | — |
|  | 5N sulfuric acid | — | — | 6 | — |
|  | Boric acid | — | — | — | 1.6 |
|  | Citric acid | — | — | — | — |
|  | Tartaric acid | — | — | — | — |
|  | Acetic acid | — | — | — | — |
|  | Lactic acid | — | — | — | — |
|  | Purified water | 19.3 | 20.2 | 18.6 | 20.1 |
|  | Total | 100 | 100 | 100 | 100 |

|  |  | Example 6 | Example 7 | Example 8 | Example 9 |
|---|---|---|---|---|---|
|  | FSH | 33.6 | 33.6 | 33.6 | 33.6 |
|  | Glycerin | 40.3 | 40.2 | 40.6 | 39.5 |
|  | Arginine | 4.5 | 4.5 | 4.5 | 4.5 |
| Acid | 5N hydrochloric acid | — | — | — | — |
|  | Phosphoric acid | — | — | — | — |
|  | 5N sulfuric acid | — | — | — | — |
|  | Boric acid | — | — | — | — |
|  | Citric acid | 1.5 | — | — | — |
|  | Tartaric acid | — | 1.6 | — | — |
|  | Acetic acid | — | — | 1 | — |
|  | Lactic acid | — | — | — | 2.6 |
|  | Purified water | 20.1 | 20.1 | 20.3 | 19.8 |
|  | Total | 100 | 100 | 100 | 100 |

The results are shown in Table 5. In coating compositions of Examples 2 to 9, a small amount of FSH aggregates was formed in coating compositions of Examples 2, 4, and 8 containing 5N hydrochloric acid, 5N sulfuric acid or acetic acid. However, no FSH aggregates were formed in Examples 3, 5 to 7 and 9.

TABLE 5

|  | Content rate of aggregates [%] |
|---|---|
| Example 2 | 11.5 |
| Example 3 | 0 |
| Example 4 | 2 |
| Example 5 | 0 |
| Example 6 | 0 |

TABLE 5-continued

|  | Content rate of aggregates [%] |
|---|---|
| Example 7 | 0 |
| Example 8 | 0.3 |
| Example 9 | 0 |

(4) Property Test 1

Coating compositions of Examples 10 to 13 and Reference Examples 10 to 12 containing FSH, glycerin, arginine, citric acid, and purified water were prepared according to the description of Table 6. Each of the obtained coating compositions was applied to the tip of each microneedle in the microneedle array by the dip method using a mask plate, and the microneedle array was dried under reduced pressure. Subsequently, the obtained microneedle device was packed and stored at 40° C. for two weeks. Thereafter, the solubility of FSH in the coating layer as well as the content rate of FSH aggregates were evaluated. In this regard, the content rate of aggregates was evaluated in a similar manner to Aggregation Test 1.

TABLE 6

|  | FSH | Glycerin | Arginine | Citric acid | Purified water |
|---|---|---|---|---|---|
| Example 10 | 100 | 120 | 7.5 | 2.5 | 30 |
| Example 11 | 100 | 120 | 15 | 5 | 30 |
| Example 12 | 100 | 120 | 30 | 10 | 30 |
| Example 13 | 100 | 120 | 60 | 20 | 30 |
| Reference Example 10 | 100 | 120 | 3 | 1 | 30 |
| Reference Example 11 | 100 | 120 | 90 | 30 | 30 |
| Reference Example 12 | 100 | 120 | 120 | 40 | 30 |

The results are shown in Table 7. In the case of the microneedle device using the coating compositions of Examples 10 to 13, the solubility of FSH in the coating layer was excellent and the formation of FSH aggregates was also suppressed. Meanwhile, in the case of using the coating composition of Reference Example 10, FSH aggregates were contained therein. In the case of using the coating compositions of Reference Examples 11 and 12, the solubility of FSH was decreased.

TABLE 7

|  | Solubility | Content rate of aggregates [%] |
|---|---|---|
| Example 10 | O | 0 |
| Example 11 | O | 0 |
| Example 12 | O | 0 |
| Example 13 | O | 0 |
| Reference Example 10 | O | 0.4 |
| Reference Example 11 | X |  |
| Reference Example 12 | X |  |

(5) Dripping Suppression Test

According to the description of Table 8, FSH, glycerin, arginine, citric acid, and purified water were mixed to prepare coating compositions of Examples 14 to 16 and Reference Example 13. The presence or absence of insoluble substances in the obtained coating compositions was visually observed. The absence of the insoluble substances was rated as "O", while the presence of the insoluble substances was rated as "X".

Each of the obtained coating compositions was applied to the tip of each microneedle in the microneedle array by the dip method using a mask plate, and the microneedle array was dried under reduced pressure to produce a microneedle device. Then, the property of the coating layer on the obtained microneedle device (presence or absence of dripping) was observed using the digital microscope (manufactured by KEYENCE CORPORATION.). The case of observation of dripping was rated as "A", while the case of non-observation of dripping was rated as "B".

TABLE 8

|  | FSH | Glycerin | Arginine | Citric acid | Purified water |
|---|---|---|---|---|---|
| Example 14 | 100 | 275 | 13.4 | 4.5 | 69 |
| Example 15 | 100 | 177 | 13.4 | 4.5 | 44 |
| Example 16 | 100 | 118 | 13.4 | 4.5 | 29 |
| Reference Example 13 | 100 | 471 | 13.4 | 4.5 | 118 |

The results are shown in Table 9. In the case of the microneedle device using the coating compositions of Examples 14 to 16, the FSH was sufficiently dissolved. Meanwhile, dripping was observed in the microneedle device using the coating composition of Reference Example 13.

TABLE 9

|  | Solubility | Property |
|---|---|---|
| Example 14 | O | A |
| Example 15 | O | A |
| Example 16 | O | A |
| Reference Example 13 | O | B |

(6) Influence by Drying

After coating microneedles with the coating composition of Example 17, the content of FSH, arginine, glycerin, and citric acid in the coating composition before drying under reduced pressure was measured by gas chromatography. Subsequently, the drying under reduced pressure was performed at room temperature and 10 Pa. Similarly, the content of FSH, arginine, glycerin, and citric acid in the coating layer was measured by gas chromatography. The coating composition of Example 17 is obtained by mixing FSH, glycerin, arginine, citric acid, and water at the percentage before drying under reduced pressure shown in Table 10.

The results are shown in Table 10. The content rate of each of the components in the coating composition before drying under reduced pressure was almost the same as that of the blending ratio of each of the components when the coating composition was prepared. Meanwhile, in the coating layer after drying under reduced pressure, not only the content rate of water but also the content rate of glycerin was decreased. Hence, glycerin evaporated together with water, as a result of which the content uniformity of FSH was excellent and dripping was further suppressed. The content rate of glycerin was further decreased by lengthening the time of drying under reduced pressure.

TABLE 10

| | Content rate [%] | | | |
|---|---|---|---|---|
|  | Before drying under reduced pressure | Drying time (15 hours) | Drying time (30 hours) | Drying time (50 hours) |
| FSH | 37.8 | 53.6 | 67.7 | 74.4 |
| Glycerin | 45.5 | 36.8 | 20 | 12.3 |
| Arginine | 5.1 | 7.2 | 9.2 | 10 |
| Citric acid | 1.7 | 2.4 | 3.1 | 3.3. |
| Water | 10 | 0 | 0 | 0 |
| Mass ratio (glycerin/FSH) | 1.2 | 0.69 | 0.3 | 0.165 |

(7) Content Uniformity Test 2

Microneedles were coated with the coating agents of Examples 18 and 19 prepared according to the description of Table 11. Each number in Table 11 means mass percent relative to the whole coating composition.

Subsequently, the coating agents of Examples 18 and 19 were applied to twenty sheets at an RH of about 40%. The coating agents applied to microneedles were respectively recovered. The content of recombinant follicle stimulating hormone (hereinafter, simply referred to as "FSH") in each of the coating agents was measured. The average, standard deviation (SD), and coefficient of variation (CV) of the content of the resulting FSH were calculated. In this regard, the coefficient of variation (CV) is a value obtained by dividing the standard deviation by the average.

TABLE 11

|  | Example 18 | Example 19 |
|---|---|---|
| FSH | 35.0 | 21.6 |
| Glycerin | 40.0 | 59.5 |
| Arginine | 5.0 | 2.9 |
| Citric acid | — | 1.0 |
| Purified water | 20.0 | 15.0 |
| Total | 100 | 100 |

The results are shown in Table 12. The coating agents of Examples 18 and 19 had a small variation in content.

TABLE 12

|  | Example 18 | Example 19 |
|---|---|---|
| Environmental humidity for coating | 40% RH | 40% RH |
| Average [µg] | 17.4 | 4.6 |
| Standard deviation (SD) [µg] | 0.7 | 0.3 |
| Coefficient of variation (CV) [%] | 3.8 | 6.3 |

(8) Aggregation Test 3

A coating agent of Example 20 was prepared according to the description of Table 13. The obtained coating agent was applied to the tip of each microneedle in the microneedle array by the dip method using a mask plate, and the microneedle array was dried under reduced pressure. Subsequently, the obtained microneedle device was packed and stored at 40° C. for two weeks. Thereafter, the content rate of the aggregates was evaluated in the following manner. In this regard, the content rate of aggregates was evaluated in a similar manner to Aggregation Test 1. No protein was contained in the fraction whose retention time was longer than that of FSH.

TABLE 13

|  | Example 20 |
| --- | --- |
| FSH | 35.0 |
| Glycerin | 40.0 |
| Arginine | 5.0 |
| Citric acid | — |
| Purified water | 20.0 |
| Total | 100 |

The content rate of aggregates in the coating agent of Example 20 was 3.8% even after being stored at 40° C. for two weeks.

(9) Property Test 2

Coating agents of Examples 21 and 22 containing FSH, glycerin, arginine, citric acid, and purified water were prepared according to the description of Table 14. Each of the obtained coating agents was applied to the tip of each microneedle in the microneedle array by the dip method using a mask plate, and the microneedle array was dried under reduced pressure. Subsequently, the obtained microneedle device was packed and stored at 40° C. for two weeks. Thereafter, the solubility of FSH in the coating layer as well as the content rate of FSH aggregates were evaluated. In this regard, the content rate of aggregates was evaluated in a similar manner to Aggregation Test 1.

TABLE 14

|  | Example 21 | Example 22 |
| --- | --- | --- |
| FSH | 100 | 100 |
| Glycerin | 120 | 120 |
| Arginine | 6 | 75 |
| Citric acid | 2 | 25 |
| Purified water | 30 | 30 |

The results are shown in Table 15. In the case of the microneedle device using the coating agents of Examples 21 and 22, the solubility of FSH in the coating layer was excellent and formation of FSH aggregates was also suppressed.

TABLE 15

|  | Solubility | Content rate of aggregates [%] |
| --- | --- | --- |
| Example 21 | O | 0.2 |
| Example 22 | O | 0 |

(10) Application of Microneedle Device

The tip of the microneedle was coated with a coating agent prepared by mixing 100 parts by mass of glycerin, 10 parts by mass of arginine, and 100 parts by mass of other components relative to 100 parts by mass of FSH, followed by drying to obtain a microneedle device. An application apparatus was used to apply the obtained microneedle device to the skin of the user. At this time, the piercing time was set at 10 seconds. The blood of the user was collected with time and the concentration of FSH in the plasma was measured.

The time (Tmax) required until the concentration of FSH in the plasma reached a maximum was about 8 hours.

REFERENCE SIGNS LIST

1 . . . Microneedle device, 2 . . . Substrate, 3 . . . Microneedle, 5 . . . Coating layer, 10 . . . Coating composition, 11 . . . Mask plate, 12 . . . Spatula, 13 . . . Opening.

The invention claimed is:

1. A microneedle device comprising:
a substrate;
a microneedle disposed on the substrate; and
a coating layer formed on the microneedle,
wherein the coating layer comprises a recombinant follicle-stimulating hormone, arginine, glycerin, and an acid selected from the group consisting of citric acid, phosphoric acid, boric acid, tartaric acid, and lactic acid,
wherein, in the coating layer, the mass of arginine is 0.13-fold of the mass of the recombinant follicle-stimulating hormone, the mass of glycerin is 0.165 to 0.69-fold of the mass of the recombinant follicle-stimulating hormone, the content of glycerin is 12.3 to 36.8 mass % based on the total amount of the coating layer, and the coating layer does not contain water.

2. A method for producing a microneedle device comprising the steps of:
providing a microneedle array having a substrate and a microneedle;
mixing a recombinant follicle-stimulating hormone, arginine, and glycerin to form a coating composition;
coating the microneedle with a coating composition; and
drying the coating composition to form a coating layer on the microneedle,
wherein, in the coating layer, the drying is performed until the mass of arginine reaches 0.13-fold of the mass of the recombinant follicle-stimulating hormone, the mass of glycerin reaches 0.165 to 0.69-fold of the mass of the recombinant follicle-stimulating hormone, the content of glycerin is 12.3 to 36.8 mass % based on the total amount of the coating layer and the content of water is reduced to 0%.

3. The method according to claim 2, wherein the coating composition further comprises an acid selected from the group consisting of citric acid, phosphoric acid, boric acid, tartaric acid, and lactic acid.

4. A microneedle device produced by the method according to claim 2.

* * * * *